United States Patent [19]

Herron et al.

[11] Patent Number: 5,237,515
[45] Date of Patent: Aug. 17, 1993

[54] METHOD OF DETERMINING ENERGY TRANSFER EFFICIENCY OF A DONOR-ACCEPTOR PAIR OF FLUORESCENT DYES

[75] Inventors: James N. Herron; Ai-Ping Wei, both of Salt Lake City, Utah

[73] Assignee: University of Utah Research Foundation, Salt Lake City, Utah

[21] Appl. No.: 683,146

[22] Filed: Apr. 10, 1991

[51] Int. Cl.⁵ .............................................. G06F 15/20
[52] U.S. Cl. ...................................... 364/498; 364/497
[58] Field of Search ................................ 364/497, 498

[56] References Cited

U.S. PATENT DOCUMENTS

| 4,666,862 | 5/1987 | Chan | 530/370 X |
| 4,996,143 | 2/1991 | Heller et al. | 436/501 X |
| 5,051,249 | 9/1991 | Metcoff | 424/9 |

OTHER PUBLICATIONS

Gennis et al; "Use of Nonspecific Dye Labeling for Singlet Energy-transfer Measurements in Complex Systems. A Simple Model": Biochemistry, vol. 11 No. 13, 1972, pp. 2509-2517.

Neter et al: "Applied Linear Regression Models"; Irwin Inc.; ISBN 0-256-070768-7; 1989 pp. xiii, 225-236.

Beebe et al: "An Introduction to Multivariate Calibration and Analysis"; Analytical Chemistry, vol. 59 No, 17, Sep. 1, 1987; pp. 1007A-1017A.

Gemperline et al: "Background Correction in Multicomponent Spectroscopic Analysis Using Target Transformation Factor Analysis"; Applied Spectroscopy; vol. 41 No. 3; 1987 pp. 454-459.

*Primary Examiner*—Edward R. Cosimano
*Attorney, Agent, or Firm*—Richard P. Fennelly; Louis A. Morris

[57] ABSTRACT

The energy transfer efficiency of a donor-acceptor pair of fluorescent dyes can be determined by first measuring the fluorescence and absorption spectra of donor-protein, acceptor-protein, mixture of donor-protein and acceptor-protein, and donor-acceptor-protein conjugates, then separating the respective spectra into their respective donor-protein complex and acceptor-protein complex components using multiple linear regression, and then determining the transfer efficiency on the basis of the quenching of the donor fluorescence based on the spectral data thus obtained.

3 Claims, 1 Drawing Sheet

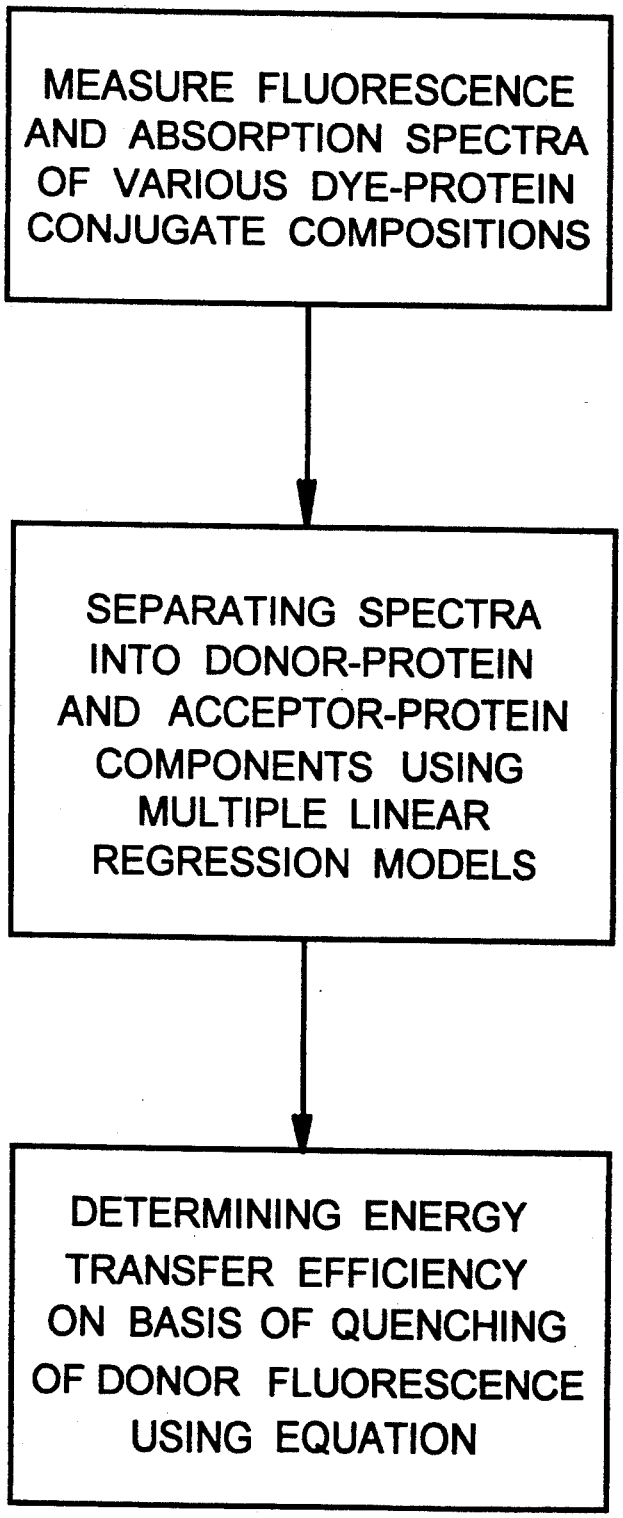

METHOD OF DETERMINING ENERGY TRANSFER EFFICIENCY OF A DONOR-ACCEPTOR PAIR OF FLUORESCENT DYES

BACKGROUND OF THE INVENTION

Fluorescent energy transfer is one mechanism which has been proposed for use in biosensor applications. In selecting optimum donor-acceptor dye pairs a number of the following criteria should be met: 1) low overlap between the absorption spectra of donor and acceptor so that the direct excitation of the acceptor by the laser line is minimal: 2) high overlap between the emission spectra of donor and absorption spectra of acceptor so that the energy transfer efficiency is maximal; 3) good separation between the emission maxima of the donor and acceptor so that the ratio of the two intensities can be taken; 4) the donor should be able to be excited with a laser; 5) the fluorescence maxima of both donor and acceptor should be at a wavelength higher than serum fluorescence; 6) both donor and acceptor should have high extinction coefficients and high fluorescence quantum yields to ensure maximum sensitivity.

In order to select optimum donor-acceptor pairs and properly characterize their fluorescence properties various aspects of the pairs and their interactions with proteins (e.g., antibodies and antigens) need to be considered including such issues as: 1) energy transfer properties in solution; 2) spectral separation to determine the energy transfer efficiency; 3) other interactions between dyes besides energy transfer; 4) better methods to determine the degree of labeling; 5) calculation of the characteristic distance for all the potential donor-acceptor pairs; 6) fluorescence lifetimes of individual donors and acceptors, as well as the donor-acceptor pairs.

It is deemed important to select respective donor and acceptor dyes on the basis of maximum energy transfer efficiency. Clearly, accurate and relatively simple analytical techniques for calculating such efficiency values would be of interest to persons using fluorescent energy transfer techniques would be of value.

Energy transfer efficiency can be calculated from either spectral or lifetime measurements. Since spectral measurements are preferred for biosensor applications, methods are needed to calculate transfer efficiency based on the spectral data. Based on the quenching of donor fluorescence, the transfer efficiency is given by:

$$E = \frac{F_d/A_d - F_d^a/A_d^a}{F_d/A_d}$$

where, E is energy transfer efficiency; $F_d$ is the fluorescence intensity of donor in the absence of acceptor; $A_d$ is the absorbance of donor in the absence of acceptor; $F^a_d$ is the fluorescence intensity of donor in the presence of acceptor; $A^a_d$ is the absorbance of donor in the presence of acceptor.

In order to calculate E, both the fluorescence and absorption spectrum of the D-A-IgG complex have to be separated into components of D-IgG and A-IgG. A curve fitting method using Gaussian distribution functions was one technique attempted to perform such a separation. It was found, however, that at least three Gaussian distributions were required to fit even a single emission peak. One would have to fit six Gaussian functions for a simple two-component system. Clearly this method was too complicated to be of any practical value.

R. B. Gennis et al. in Biochemistry, Vol. 11, No. 13, 1972, 2509–2517 mention the following ways in which transfer efficiencies might be calculated: (1) numerical integration; (2) an equation, as depicted in its Appendix, involving two donors and one acceptor; and (3) Markov chain methods.

DESCRIPTION OF THE DRAWING

The drawing, which forms a portion of the specification, is a flow diagram of the method of the present invention.

DESCRIPTION OF THE INVENTION

The present invention is directed to a method of determining the energy transfer efficiency of such donor-acceptor pair of fluorescent dyes by measuring the fluorescence and absorption spectra of a donor(D)-acceptor(A)-protein (e.g., IgG) complex, separating the respective spectra thereby measured into its donor-protein (e.g., donor-protein such as donor(D)-IgG) and acceptor-protein components using standard multiple linear regression analysis, and determining the transfer efficiency therefrom on the basis of the quenching of donor fluorescence using the equation for E given above.

In accordance with the present invention it was found that the respective spectra (the fluorescence and absorption spectra of the donor-protein and acceptor-protein complexes) can be separated from the respective donor-acceptor-protein spectra by using a multiple linear regression technique based on the following model (in the case of fluorescence spectra):

$$F_{a\text{-}d} = \alpha \cdot F_d + \beta \cdot F_a + \epsilon$$

where, $F_d$, $F_a$, $F_{a\text{-}d}$ are the fluorescence spectra of the donor-protein conjugate, the acceptor protein conjugate, and the donor-acceptor-protein conjugate, respectively, $\alpha$, and $\beta$ are the linear coefficients to be determined, and $\epsilon$ is the error term which is usually under 1%. An analogous model is used for the absorption spectra. Moreover, the coefficient of determination ($>0.99$) also indicates that the model equation given above produces an excellent fit with experimental results.

In accordance with the present invention, the fluorescence spectra of immunoglobulins labeled with donor (e.g., fluorescein-IgG), acceptor (e.g., rhodamine B-IgG), and colabeled with both donor and acceptor (e.g., fluorescein-IgG-rhodamine B) were subject to factor analysis in order to determine the interaction components between the donor and acceptor dyes. This is very important because as concentration of the dye-IgG increases, the interaction between dyes (self-absorption and trivial reabsorption) become significant. This situation is most likely to occur at an interface between aqueous solution and solid substrate, when the competitive immuno binding reactions occur in biosensor applications. Once the interaction components are determined, they can be incorporated into equation (1) as additional components for multiple linear regression. Therefore, this procedure is of significance for improving the accuracy and sensitivity of biosensors.

The step of determining the interaction components between donor and acceptor by multivariate factor analysis is also an important feature of the present invention. These interactions are significant for biosensor applications because most biosensor designs involve immuno reactions at the surfaces of solid substrate where increased intermolecular and intramolecular interactions can occur. Once the analytical function of the interaction components can then be incorporated into the multiple linear regression model as an additional term. This procedure will contribute to the development of accurate and sensitive biosensors.

The foregoing invention is further illustrated by the Example in which the energy transfer efficiency from fluorescein to rhodamine B was determined.

EXAMPLE

In the first step, rhodamine B isocyanate (Research Organics, New York) and 5-, 6-carboxylfluorescein succinimidyl ester (Molecular Probes, Inc., Eugene, OR) were reacted, respectively, with mouse immunoglobulins (Cappel, Organon Teknika Corporation) in 50 mM phosphate buffer, pH 7.7, for about 12 hours at room temperature. The rhodamine B-IgG conjugates (RB-IgG) were separated from the unreacted dyes using a PD-10 gel filtration chromatography column (Pharmacia LKB, Piscataway, N.J.). F and RB-colabeled IgG (F-RB-IgG) were prepared by reacting equal molar ratios of rhodamine B isocyocynate and 5-, 6-carboxylfluorescein succinimidyl ester with IgG under the same conditions.

In the second step, the UV-VIS absorption spectra and fluorescence spectra of the F-IgG, RB-IgG, F-RB-IgG conjugates and the mixture of F-IgG and RB-IgG were measured at several different concentrations.

In the third step, a 176×17 matrix was constructed from 17 emission spectra (F-IgG, RB-IgG and RB-IgG mixtures, and F-RB-IgG). Factor analysis was performed using the statistical software package Number Cruncher Statistical System (NCSS, Kaysville, Utah) on a IBM PC. Four significant factors were identified by the factor analysis. The four factors accounted for 99.62% of the original variations. The first two factors (components) were the emission spectra of fluorescein and rhodamine B, respectively, and accounted for 98.62% of the original variations. The third factor varied with the intensity of the signal, and was attributed to electrical noise in the detection system. The fourth factor was correlated to the absorption spectrum of rhodamine B and was due to the interaction between donor (F) and acceptor (RB) through trivial reabsorption.

The transfer efficiency calculated according to the foregoing equation indicates that 94% of the fluorescence of the fluorescein was transferred to rhodamine B, while there was little increase in rhodamine B fluorescence. This result suggests that the fluorescein-rhodamine B pair is a "dark" transfer pair.

We claim:

1. A method of determining the energy transfer efficiency of a donor-acceptor pair of fluorescent dyes useful in fluorescent energy transfer immunoassay which comprises:
   (a) measuring the fluorescence and absorption spectra of donor-protein, acceptor-protein, mixture of donor-protein and acceptor-protein and donor-acceptor-protein conjugates;
   (b) separating the respective spectra measured in (a) into their respective donor-protein complex and acceptor-protein complex components using multiple linear regression and employing models $$F_{a\text{-}d} = \alpha \cdot F_d + \beta \cdot F_a + \epsilon$$

and $$A_{a\text{-}d} = \alpha' \cdot A_d + \beta' \cdot A_a + \epsilon'$$

where $F_d$, $F_a$, and $F_{a\text{-}d}$ are the fluorescence spectra of the donor-protein conjugate, the acceptor-protein conjugate, and the donor-acceptor-protein conjugate, respectively, $\alpha$ and $\beta$ are the linear coefficients to be determined and $\epsilon$ is the error term and $A_d$, $A_a$, and $A_{a\text{-}d}$ are the absorption spectra of the donor-protein conjugate, the acceptor-protein conjugate, and the donor-acceptor-protein conjugate, respectively, $\alpha'$ and $\beta'$ are the linear coefficients to be determined and $\epsilon'$ is the error term; and
   (c) determining the energy transfer efficiency on the basis of quenching of donor fluorescence using the equation $$E = \frac{F_d/A_d - F_d^a/A_d^a}{F_d/A_d}$$

where E is energy transfer efficiency, $F_d$ is the fluorescence intensity of donor in the absence of acceptor, $A_d$ is the absorbance of donor in the absence of acceptor, $F_d^a$ is the fluorescence intensity of the donor in the presence of acceptor, and $A_d^a$ is the absorbance of donor in the presence of acceptor.

2. A method as claimed in Claim 1 wherein the interaction components between donor and acceptor are also determined by multivariate factor analysis and these interaction components are incorporated into the step (b) multiple linear regression.

3. A method as claimed in claim 2 wherein the interaction components between donor and acceptor was determined by multivariate factor analysis using a data matrix consisting of fluorescence spectra of the donor-protein, acceptor-protein, mixture of donor-protein and acceptor-protein, and donor-acceptor-protein conjugates.

* * * * *